(12) United States Patent
Alexander et al.

(10) Patent No.: US 10,723,744 B2
(45) Date of Patent: *Jul. 28, 2020

(54) TRANSPLANTATION THERAPIES

(71) Applicants: Aphios Corporation, Woburn, MA (US); For the Board of Supervisors of Louisiana State University and Agricultural and Mechanical College, Baton Rouge, LA (US)

(72) Inventors: Jonathan Steven Alexander, Shreveport, LA (US); April C. Carpenter, Cincinnati, OH (US); Trevor Percival Castor, Arlington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/004,039

(22) Filed: Jun. 8, 2018

(65) Prior Publication Data

US 2018/0291033 A1 Oct. 11, 2018

Related U.S. Application Data

(60) Division of application No. 14/502,311, filed on Sep. 30, 2014, now Pat. No. 9,994,585, which is a continuation-in-part of application No. 13/355,256, filed on Jan. 20, 2012, now abandoned, which is a continuation-in-part of application No. 12/319,004, filed on Dec. 31, 2008, now abandoned.

(60) Provisional application No. 61/009,645, filed on Dec. 31, 2007.

(51) Int. Cl.
  *A61K 31/365* (2006.01)
  *A61K 47/14* (2017.01)
  *A61P 37/06* (2006.01)
  *C07D 493/22* (2006.01)

(52) U.S. Cl.
  CPC .......... *C07D 493/22* (2013.01); *A61K 31/365* (2013.01); *A61K 47/14* (2013.01); *A61P 37/06* (2018.01)

(58) Field of Classification Search
  CPC ........ A61K 31/365; A61K 47/14; A61P 37/06
  See application file for complete search history.

(56) References Cited

U.S. PATENT DOCUMENTS

| | | | |
|---|---|---|---|
| 3,288,824 A * | 11/1966 | Mahler | A01N 25/30 106/18 |
| 4,560,774 A | 12/1985 | Pettit et al. | |
| 4,611,066 A | 9/1986 | Pettit et al. | |
| 5,641,745 A | 6/1997 | Ramtoola | |
| 5,736,542 A | 4/1998 | Henry et al. | |
| 5,750,709 A | 5/1998 | Castor | |
| 5,854,064 A | 12/1998 | Castor et al. | |
| 5,932,243 A * | 8/1999 | Fricker | A61K 9/1075 424/400 |
| 6,221,153 B1 | 4/2001 | Castor et al. | |
| 6,228,843 B1 | 5/2001 | Dempsey | |
| 6,407,058 B1 | 6/2002 | Staddon et al. | |
| 6,624,189 B2 | 9/2003 | Wender et al. | |
| 9,034,347 B2 | 5/2015 | Castor et al. | |
| 9,994,585 B2 | 6/2018 | Alexander et al. | |
| 2001/0003589 A1 * | 6/2001 | Neuer | A61K 9/4858 424/456 |
| 2002/0061303 A1 | 5/2002 | Singh | |
| 2003/0171356 A1 | 9/2003 | Etcheberrigaray et al. | |
| 2003/0199469 A1 | 10/2003 | Schwartz et al. | |
| 2003/0216303 A1 * | 11/2003 | Ambuhl | A61K 9/1075 514/772.4 |
| 2006/0165987 A1 | 7/2006 | Hildgen et al. | |
| 2007/0190163 A1 | 8/2007 | Malaknov et al. | |
| 2008/0004332 A1 | 1/2008 | Alkon | |
| 2008/0207742 A1 | 8/2008 | Zohar et al. | |
| 2009/0270492 A1 | 10/2009 | Wender | |
| 2009/0306225 A1 | 12/2009 | Lichter et al. | |
| 2010/0166806 A1 | 7/2010 | Castor | |
| 2010/0168219 A1 | 7/2010 | Alexander | |
| 2011/0129450 A1 | 6/2011 | Lazarov et al. | |
| 2012/0309818 A1 | 12/2012 | Alexander et al. | |
| 2013/0072550 A1 | 3/2013 | Etcheberrigaray et al. | |
| 2015/0246000 A1 | 9/2015 | Castor et al. | |
| 2015/0291616 A1 | 10/2015 | Castor | |
| 2015/0297555 A1 | 10/2015 | Castor | |

FOREIGN PATENT DOCUMENTS

| | | |
|---|---|---|
| CN | 1678304 A | 10/2005 |
| WO | 2004/004641 A2 | 1/2004 |
| WO | 2009/129361 A2 | 10/2009 |
| WO | 2010/144499 A2 | 12/2010 |
| WO | 2013/071282 A1 | 5/2013 |

OTHER PUBLICATIONS

Pettit, G., Herald, C. L., Kamano, Y., Gust, D., & Aoyagi, R. (1983). The structure of bryostatin 2 from the marine Bryozoan Bugula neritina. Journal of Natural Products, 46(4), 528-531. (Year: 1983).*
Prendiville et al., "A phase I study of intravenous bryostatin 1 in patients with advanced cancer," Br. J. Cancer Aug. 1993; 68(2): 418-24. PMID: 8347500; PubMed Central PMCID: PMC1968558. (Year: 1993).*
U.S. Appl. No. 14/647,237, filed May 26, 2015, Published.
U.S. Appl. No. 14/646,817, filed May 22, 2015, Published.
U.S. Appl. No. 12/319,004, filed Dec. 31, 2008, Abandon.
U.S. Appl. No. 13/355,256, filed Jan. 20, 2012, Abandon.
U.S. Appl. No. 14/502,311, filed Sep. 30, 2014, Granted.
U.S. Appl. No. 13/720,157, filed Dec. 19, 2012, Granted.

(Continued)

*Primary Examiner* — Theodore R. West (57) ABSTRACT

Embodiments of the present invention are directed to methods and dosage forms for treating inflammation and rejection in transplantation injuries with Bryostatin-1, Bryostatin-1 analogs and pharmaceutically acceptable salts thereof.

17 Claims, 10 Drawing Sheets

(56) References Cited

OTHER PUBLICATIONS

U.S. Appl. No. 14/714,433, filed May 18, 2015, Granted.
Carpenter et al., Endothelial PKC delta activation attenuates neutrophil transendothelial migration. Inflamm Res. May 2008;57(5):216-29.
Dale et al., Comparison of effects of bryostatins 1 and 2 and 12-O-tetradecanoylphorbol-13-acetate on protein kinase C activity in A549 human lung carcinoma cells. Cancer Res. Jun. 15, 1989;49(12):3242-5.
Hale et al., The chemistry and biology of the bryostatin antitumor macrolides. Natural Product Reports. 2002;19(4):413-453.
Healy et al., Neutrophil transendothelial migration potential predicts rejection severity in human cardiac transplantation. Eur J Cardiothorac Surg. May 2006;29(5):760-6.
Jordan et al., The role of neutrophils in myocardial ischemia-reperfusion injury. Cardiovasc Res. Sep. 1999;43(4):860-78.
Koryakina et al., Regulation of secretases by all-trans-retinoic acid. FEBS J. May 2009;276(9):2645-2655.
Lopanik et al., Structure of bryostatin 20: a symbiont-produced chemical defense for larvae of the host bryozoan, Bugula neritina. J Nat Prod. Aug. 2004;67(8):1412-4.
Manning, Identifying byrostatins and potential precursors from the bryozoan Bugula neritina. Natural Product Research. 2005;19:467-491.
Mehla et al., Bryostatin modulates latent HIV-1 infection via PKC and AMPK signaling but inhibits acute infection in a receptor independent manner. PLoS One. Jun. 16, 2010;5(6):e11160. 15 pages.
Moreno et al., Neovascularization in human atherosclerosis. Circulation. May 9, 2006;113(18):2245-52.
Pettit et al., Antineoplastic Agents 100. The Marine Bryozoan Amathia Convoluta. Tetrahedron. 1985;41(6):985-994.
Pettit et al., Antineoplastic agents. 340. Isolation and structural elucidation of bryostatins 16-18. J Nat Prod. Mar. 1996;59(3):286-9.
Pettit et al., Isolation and Structure of Bryostatin 1. J Am Chem Soc. 1982;104:6846-6848.
Pettit et al., Isolation and structure of bryostatin 9. J Nat Prod. Jul.-Aug. 1986;49(4):661-4.
Pettit et al., Isolation and Structure of Bryostatins 10 and 11. J Org Chem. 1987;52:2848-2854.
Pettit et al., Isolation and Structure of Bryostatins 12 and 13. J Org Chem. 1987;52:2854-2860.
Pettit et al., Isolation and Structure of Bryostatins 14 and 15. Tetrahedron. 1991;47(22):3601-3610.
Pettit et al., Isolation and structure of bryostatins 5-7. Can J Chem. 1985;63:1204-1208.
Pettit et al., Structure of Bryostatin 4. An Important Antineoplastic Constituent of Geographically Diverse *Bugula neritina* (Bryozoa). J Am Chem Soc. 1984;106:6768-6771.
Pettit et al., Structure of the *Bugula neritina* (Marine Bryozoa) Antineoplastic Component Bryostatin 3. J Org Chem. 1983;48:5354-5356.
Pettit et al., The Structure of Bryostatin 2 from the Marine Bryozoan Bugula Neritina. Journal of Natural Products. Jul.-Aug. 1983;46(4):528-531.
Sodhi et al., All-trans retinoic acid rescues memory deficits and neuropathological changes in mouse model of streptozotocin-induced dementia of Alzheimer's type. Prog Neuropsychopharmacol Biol Psychiatry. Jan. 10, 2013;40:38-46.
Stone et al., A phase IIb trial of all-trans retinoic acid (ATRA) combined with bryostatin 1 (BRYO) in patients (pts) with myelodysplastic syndromes (MDS) and acute myeloid leukemia (AML). Blood. 2000;96(11, Part 2):265b, 42nd Annual Meeting of the American Society of Hematology, (abstract) BIOSIS [online] [retrieved on Oct. 8, 2017] BIOSIS.
Stone et al., The Combination of All-Trans Retinoic Acid (Atra) and Bryostatin 1 (Bryo) Induces Monocytic Differentiation (MD) in Human Myeloid Leukemia Leukemia Research. 1997;21(1):S24, Poster Presentation No. 93. 1 page.

\* cited by examiner

TRANSPLANTATION THERAPIES

CROSS-REFERENCE TO RELATED APPLICATIONS

This Application is a divisional of U.S. patent application Ser. No. 14/502,311, filed Sep. 30, 2014, now U.S. Pat. No. 9,994,585, which is a continuation in part and claims priority to U.S. patent application Ser. No. 13/355,256 filed Jan. 20, 2012, which is a continuation in part of and claims priority to U.S. patent application Ser. No. 12/319,004, filed Dec. 31, 2008, which claims priority to U.S. Provisional Patent Application Ser. No. 61/009,645, filed Dec. 31, 2007, all of which are hereby incorporated by reference in their entirety.

GOVERNMENT SUPPORT

Research leading to this invention was in part funded with Grant No. NIH DK-43785 from the National Institutes of Health, Bethesda, Md., USA.

FIELD OF INVENTION

Embodiments of the present invention are directed to methods and dosage forms for treating transplantation mediated organ stress and rejection.

BACKGROUND OF THE INVENTION

Leukocyte dependent injury is an important aspect of acute and chronic inflammatory disease processes caused by transplantation. It would be desirable to have therapies which reduce neutrophil infiltration into transplanted organs and tissue to reduce inflammation and rejection.

For the purpose of the present discussion the following terms will be defined as set forth below unless the context in which the term is used establishes a different meaning or such different meaning is required.

As used herein the term "dosage form" is a means for administering a drug and includes orally administered drugs forms, parenteral drug forms or formulations, implantable devices and forms, topical forms such as transdermal patches, powders, sprays, creams and ointments, and intranasal and ophthalmic preparations. An example of an oral dosage form comprises, without limitation, tablets, capsules, powders, lozenges, troches or liquids for ingestion or sublingual or buccal absorption. Examples of a "pharmaceutical parenteral formulation" comprise, without limitation, a sterile, isotonically acceptable and pH acceptable, aqueous solution, emulsion or suspension of a drug for direct injection into the body or for perfusing one or more organs.

As used herein, the term "pharmaceutically acceptable salt" means a drug that has been modified to present a salt of physiologically acceptable anion or cation.

Bryostatin-1 is used in its conventional scientific meaning to encompass Bryostatin-1 or any compound which is based on the Bryostatin structural backbone. As used herein, the term "Bryostatin-1 analog" means a composition having the general formula of Brystatin-1 with substitutions comprising methyl or ethyl groups or halogens and ammonium groups which do not substantially alter the biological activity of the composition.

BRIEF SUMMARY OF THE INVENTION

Embodiments of the present invention are directed to therapies for treating transplantation mediated organ stress and rejection. One embodiment, directed to a method of treating or preventing transplantation injury, comprises the steps of administering an effective amount of Bryostatin-1, Bryostatin-1 analog or a pharmaceutically acceptable salt thereof to reduce or prevent induced neutrophil trans endothelial migration.

As used herein, an effective amount is such an amount needed to achieve the desired result. One effective amount is such an amount to achieve a plasma concentration in an individual being treated for transplantation injury or in tissue or organ being prepared for transplantation in the range of $10^{-9}$ to $10^{-6}$M, or move preferably, about $10^{-7}$M. As used herein, the term "individual" encompasses a human or an animal subject. For organ or tissue perfusion, this amount is 100 micrograms per kg of tissue or organ mass for a concentration of $10^{-7}$M.

The effective amount of Bryostatin-1, Bryostatin-1 analog or a pharmaceutically acceptable salt thereof is preferably held in a dosage form. One preferred dosage form is suitable for oral administration. One oral dosage form is a solid oral dosage form.

One method features a solid dosage form that presents an effective amount of Bryostatin-1, Bryostatin-1 analog or a pharmaceutically acceptable salt thereof dispersed or dissolved in a saturated polyalkylene glycol glyceride. One saturated polyalkylene glycol glyceride is a mixture of polyalkylene esters of one or more eight carbons to eighteen carbons saturated fatty acids with glycerol. One polyalkylene glycol features a polyethylene glycol having a molecular weight of 1,000 to 2,000 daltons, and another features a molecular weight of 1,400 to 1,600 daltons.

One method features Bryostatin-1, Bryostatin-1 analog or a pharmaceutically acceptable salt thereof present in an oral dosage form in an amount of 1 to 30% by weight or, more preferably, in an amount of 10 to 20%.

One embodiment of the method features an effective amount of Bryostatin-1, Bryostatin-1 analog or a pharmaceutically acceptable salt in a parenteral formulation. Embodiments of such a pharmaceutical preparation are formulated in polyalkylene glycol glycerides. One embodiment of the polyalkylene glycol glyceride is a mixture of polyalkylene esters of one or more eight carbons to eighteen carbons saturated fatty acids with glycerol. One embodiment features a polyalkylene glycol that is a polyethylene glycol having a molecular weight of 1,000 to 2,000 daltons.

One embodiment of the method features Bryostatin-1, Bryostatin-1 analog or pharmaceutically acceptable salt thereof present in a formulation at an amount of 1 to 30% Bryostatin-1 by weight or 10 to 20% by weight.

One embodiment of the method features Bryostatin-1, Bryostatin-1 analog or pharmaceutically acceptable salt thereof in a parenteral formulation as a dispersion in water having a concentration of 0.0005 to 0.5% by weight.

A further embodiment of the present invention is drawn to a dosage form. One dosage form in accordance with the present invention features an effective amount of Bryostatin-1, Bryostatin-1 analog or a pharmaceutically acceptable salt thereof used as a pre- or co-treatment to reduce or prevent transplantation stress induced neutrophil trans endothelial migration via PKC-δ activation to stabilize the vasculature against the penetration of leukocytes into the target organ as a treatment for transplantation injury. An effective amount is such an amount needed to achieve the desired result. One effective amount is such an amount to achieve a plasma concentration in the range of $10^{-6}$ to $10^{-9}$M Bryostatin-1, Bryostatin-1 analog or pharmaceutically acceptable salt thereof or preferably in an individual being treated for transplantation injury or in tissue or organ being prepared for transplantation. As used herein, the term "individual" encompasses a human or an animal subject. For organ or tissue perfusion, this amount is 100 micrograms per kg of tissue or organ mass for a concentration of $10^{-7}$M.

The dosage form may take several forms. A solid oral dosage form or a pharmaceutically acceptable salt thereof is dispersed or dissolved in a saturated polyalkylene glycol glyceride.

One embodiment of the dosage form features a polyalkylene glycol glyceride which is a mixture of polyalkylene esters of one or more eight carbons to eighteen carbons saturated fatty acids with glycerol. A further embodiment features a polyalkylene glycol comprising a polyethylene glycol having a molecular weight of 1,000 to 2,000 daltons, and with more specificity, a molecular weight of 1,400 to 1,600 daltons.

One embodiment features Bryostatin-1, Bryostatin-1 analog or pharmaceutically acceptable salt thereof in an oral dosage form in an amount of 1 to 30% by weight, or with greater specificity, or in an amount of 10 to 20% by weight.

One embodiment of the dosage form features a pharmaceutical parenteral formulation do not accept change to comprising polyalkylene glycol glycerides. One polyalkylene glycol glyceride is a mixture of polyalkylene esters of one or more eight carbons to eighteen carbons saturated fatty acids with glycerol. And, one embodiment features a polyalkylene glycol comprising a polyethylene glycol having a molecular weight of 1,000 to 2,000 daltons, and with greater specificity, a molecular weight of 1,400 to 1,600 daltons.

One parenteral formulation of the present invention features Bryostatin-1, Bryostatin-1 analog or pharmaceutically acceptable salt thereof is present in an amount of 1 to 30% by weight or with greater specificity, in an amount of 10 to 20% by weight.

One parenteral formulation of the present invention features Bryostatin-1, Bryostatin-1 analog or pharmaceutically acceptable salt thereof present in the pharmaceutical parenteral formulation as a dispersion in water having a concentration of 0.0005 to 0.5% by weight.

These and other features and advantages will be apparent to those skilled in the art upon viewing the figures and drawings which are briefly described below and upon reading the detailed description that follows.

BRIEF DESCRIPTION OF THE DRAWINGS

FIG. 9 is a photomicrograph of a gel that depicts siRNA knockdown of specific PKC isoforms; and, FIG. 10 contains two graphs which demonstrate that Bryostatin-1 will not inhibit $LTB_4$ mediated neutrophil migration in PKC-δ siRNA nucleofected (PKC-δ blocked) HUVEC (right panel), but still suppresses migration in PKC-ε siRNA nucleofected (PKC-ε blocked) HUVEC (left panel).

DETAILED DESCRIPTION OF THE INVENTION

Neutrophil mediated tissue injury is a feature of both acute and chronic inflammatory disease processes. Methods to reduce neutrophil infiltration could provide therapies in numerous diseases including stroke, inflammatory bowel disease, arthritis, arteriosclerosis and graft vs. host disease (GVHD). Generally the vascular endothelium exists in a quiescent state, without supporting leukocyte rolling, adhesion, or transmigration. In vitro there is consistent and reproducible evidence suggesting that under non-inflamed conditions an almost insignificant amount of neutrophil trans endothelial migration takes play through an unstimulated endothelial monolayer. However, in the presence of an exogenously applied chemoattractant, or upon endothelial activation (e.g. with Th1 cytokines, LPS), significant quantities of neutrophils will migrate through endothelial monolayers into tissues, often causing bystander tissue injury.

Leukocyte transmigration is usually described as a three-step process involving: 1) rolling along the endothelium 2) firm adhesion to the endothelium and lastly 3) migration across the endothelial monolayer into underlying tissues. The process of trans endothelial migration begins when the leukocytes first undergo selectin-mediated rolling followed by integrin-mediated firm adhesion. The first two steps are mechanistically well-characterized and result in the accumulation of leukocytes on the luminal surface of vascular endothelial cells.

Leukocyte-endothelial signaling through adhesion molecules and integrins during these steps is important for the final stage of trans endothelial migration (TEM) or 'diapedesis' (movement out of blood vessels into tissues) involving migration of the neutrophil in an amoeboid manner through the endothelial monolayer followed by leukocyte migration within the interstitium. The current general paradigm suggests that neutrophil migration occurs at endothelial cell-cell junctions and is mediated by endothelial cell adhesion molecule (ECAM) interactions including intercellular adhesion molecule-1 (ICAM-1), platelet endothelial cell adhesion molecule-1 (PECAM-1), CD99, lymphocyte specific protein-1 (LSP-1), and inhibitor of apoptosis (IAP). However, the role of endothelial second messengers and their possible regulation of neutrophil migration have not been investigated as extensively.

At least two distinct forms of leukocyte migration are recognized during inflammation: acute, chemoattractant mediated transmigration (Type I) and chronic or cytokine-activated transmigration (Type II). Type I requires only a gradient of chemotactic factors such as leukotriene B4 ($LTB_4$), platelet activating factor (PAF), or n-formyl-met-leu-phe (fMLP), and has reported to be independent of PECAM-1 (an adhesion molecule suggested to mediate leukocyte trans endothelial migration), despite the presence of PECAM-1 on both neutrophils and endothelial cells. This type of migration usually takes only minutes to activate, lasts for hours and does not require protein synthesis. In contrast, type II migration is 'chronic' and requires prior 'activation' of the endothelium by cytokines. Type II migration relies on transcription and synthesis of ECAM proteins and several other inflammatory chemoattractants e.g. chemokines. While Type II migration can almost totally be abolished by PECAM-1 blockade, PECAM-1 plays no role in Type I TEM. Studies performed in vitro and in vivo characterizing the involvement of both endothelial cell-cell junctions and endothelial cell adhesion molecules in PMN transmigration have been discussed in several reviews.

While neutrophil products may alter endothelial junctional and increase endothelial permeability, neutrophil extravasation and vascular permeability regulation are independently controlled processes. Interestingly though, there is some overlap in factors mediating permeability (histamine, thrombin) and endothelial signals produced by neutrophil adhesion such as $Ca^{++}$, mitogen activated protein kinase (MAPK), extracellular signal-regulated kinase (ERK), and myosin light chain kinase. Due to the fact that increased vascular (endothelial) monolayer permeability and formation of junctional gaps (through which neutrophils pass) are often assumed to be distinct features of acute inflammation, numerous researchers have investigated the role of these second messengers and the function of the endothelial cell contractile apparatus in the modulation of neutrophil migration.

Numerous signals are initiated upon neutrophil binding to endothelial monolayers that has been suggested to promote changes in the contractile state of the cell and result in junctional alteration increasing PMN TEM. One of the first is a transient increase in intracellular free calcium. The next step in this process is the activation of myosin light chain kinase leading to phosphorylation of myosin light chains resulting in increased isometric tension. The final effect is a relaxation of endothelial junctional contacts, endothelial retraction, and the formation of subsequent space facilitating neutrophil passage.

These observations have led to studies on the outcomes of inhibiting these second messengers on neutrophil migration in response to various substances. It has been reported that endothelial cytoskeletal alterations could change PMN TEM in response to fMLP. This was further supported by studies using the blockade of intracellular calcium release and myosin light chain kinase in the endothelium to inhibit neutrophil migration in response to $LTB_4$ gradients. Enhanced intracellular $Ca^{++}$ has been suggested to be essential for myosin light chain phosphorylation and thus gap formation between endothelial cells. In addition to $Ca^{++}$, Rho kinase blockade upstream of MLC phosphorylation as well as actin polymerization has been implicated in inhibition of neutrophil TEM in response to $LTB_4$ through interactions with MLC phosphatase. Moreover MAPK/ERK1/2 activation has also been suggested to regulate neutrophil TEM in response to both an fMLP gradient and activation of the endothelium by TNF-α.

Consequently, several potential endothelial second messengers have been investigated in the control of neutrophil migration. We therefore set out to define other less evident second messengers that could alter neutrophil TEM in response to $LTB_4$ and TNF-α. We screened activation and inhibition of a variety of endothelial second messengers and found the most dramatic effects with PKC-δ activators. Our studies suggest activation of specifically PKC-δ, but not PKC-α can inhibit neutrophil trans endothelial migration in response to both $LTB_4$ and TNF-α. In addition, our studies suggest that even a short-term activation of PKC-δ can inhibit PMN TEM for long periods of time, up to 48 hours, without affecting endothelial viability. We therefore suggest PKC-δ activation may be therapeutically beneficial in numerous inflammatory disorders.

In addition to organ transplantation, Graft-versus-host disease (GVHD) is another clinical scenario which could be favorably affected by Bryostatin-1 suppression of leukocyte extravasation. GVHD is a serious complication that often occurs after a stem cell or bone marrow transplantation (BMT) where the recently transplanted bone marrow mounts an attack against the transplant recipient's tissue. GVHD often produces severe host inflammatory reactions against several host tissues, (liver, lung, skin and gastrointestinal tract) with intense systemic inflammation, severe morbidity and mortality.

Although cells within the adaptive immune system contribute to GVHD, neutrophils are now known to also contribute to the severity of this condition. Currently, glucocorticoids are the standard treatment for chronic GVHD, and outcomes remain unsatisfactory, especially in high-risk patients. Other treatments for chronic GVHD include rituximab, sirolimus, mycofenolate mofetil, imatinib and pentostatin. While restoration of neutrophils is considered to be essential to BMT success, neutrophils also contribute to GVHD severity. While granulocyte colony stimulating factor (G-CSF) is used to re-engraft neutrophils, researchers recently found unexpectedly that G-CSF worsened acute GVHD in peripheral blood stem cell recipients and enhanced chronic GVHD in bone marrow recipients consistent with neutrophil extravasation intensifying the severity of GVHD. Scientists have shown that the transplant rejection mortality rate at 90 days following engrafting was associated with an increased presence of neutrophils in intestinal biopsies, and that the liver was another important target of this type of injury. Additionally, BMT can also promote lung injury after BMT in a neutrophil-dependent fashion. Because we have found that low-dose treatment with Bryostatin-1 limits neutrophil chemotaxis and extravasation, it can have important applications in the suppression of GVHD following BMT. Because adaptive immune cells also utilize the same molecular mechanisms as neutrophils (selectins, ICAM-1 and related IgCAM adhesion molecules, CD99, etc.) to penetrate tissues during inflammation, Bryostatin-1 is anticipated to also interfere with inflammatory escape of adaptive immune cells (T-cells, monocytes) into tissues following BMT, further reducing the incidence of GVHD.

The method for treating inflammatory disease and transplantation according to the invention is characterized in that it includes: (i) the perfusion of organs with Bryostatin-1 or one of its derivatives under conditions which permits vascular selective exposure to these compounds prior to or immediately following organ 'harvesting', and (ii) intravenous, transdermal, intraperitoneal, intra-alveolar instillation of Bryostatin-1 or one of its derivatives in vivo during active disease, or during periods of disease remission and (iii) prophylactic administration of Bryostatin-1 or one of its derivatives to limit the development of GVHD.

Figure 1:
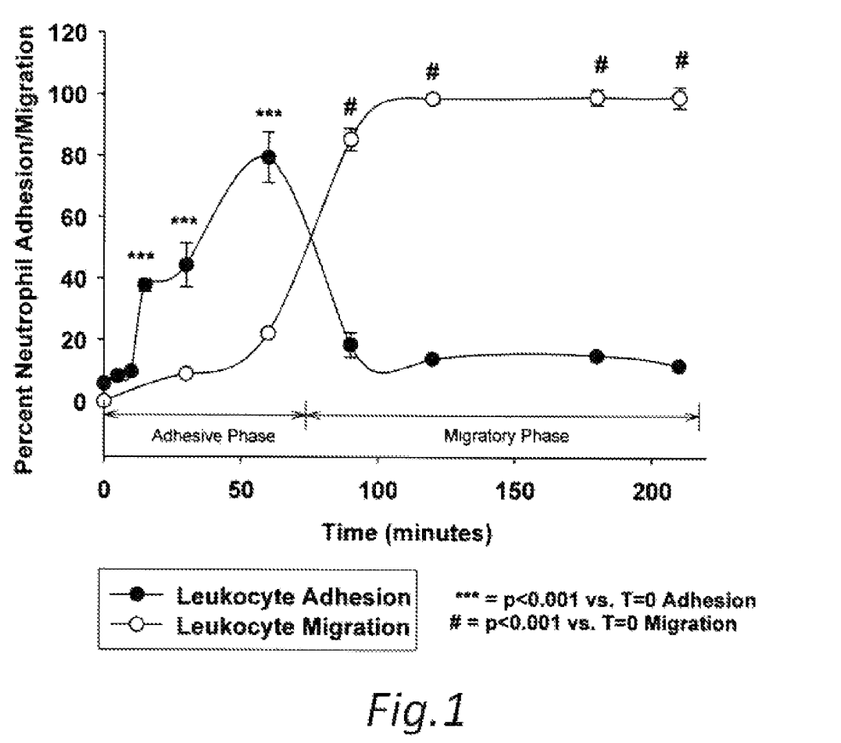
FIG. 1 is a graph depicting neutrophil adhesion to and migration across human microvascular endothelial cell HMEC (monolayers) upon stimulation with a chemoattractant $LTB_4$ over time in a two-chamber chemotaxis study.

Turning now to FIG. 1, FIG. 1 graphically depicts neutrophil adhesion to and migration through human microvascular endothelial cell monolayers (HMECs) in a two compartment system upon administration of an $LTB_4$ gradient in the lower chamber over time. HMECs were plated on porous 8 μm (micron) transwell two-chamber inserts and allowed to reach confluency for migration assays. For the adhesion assay, HMECs were plated on 48-well plates. 100 nM $LTB_4$ and 500,000 neutrophils were added to the upper compartment to initiate adhesion, while 500,000 neutrophils were added to the upper compartment and $LTB_4$ to the lower compartment to initiate migration. Both neutrophil adhesion and migration were measured over 3 h and expressed as % change in adhesion and the fraction of migrated cells in chemoattractant stimulated experiments vs. controls which had no chemoattractant added. An inverse relationship was observed between adhesion and migration with maximal significant adhesion observed at 1 h (*p<0.001) and maximally significant migration observed by 2 h. (*p<0.001).

Figure 2:
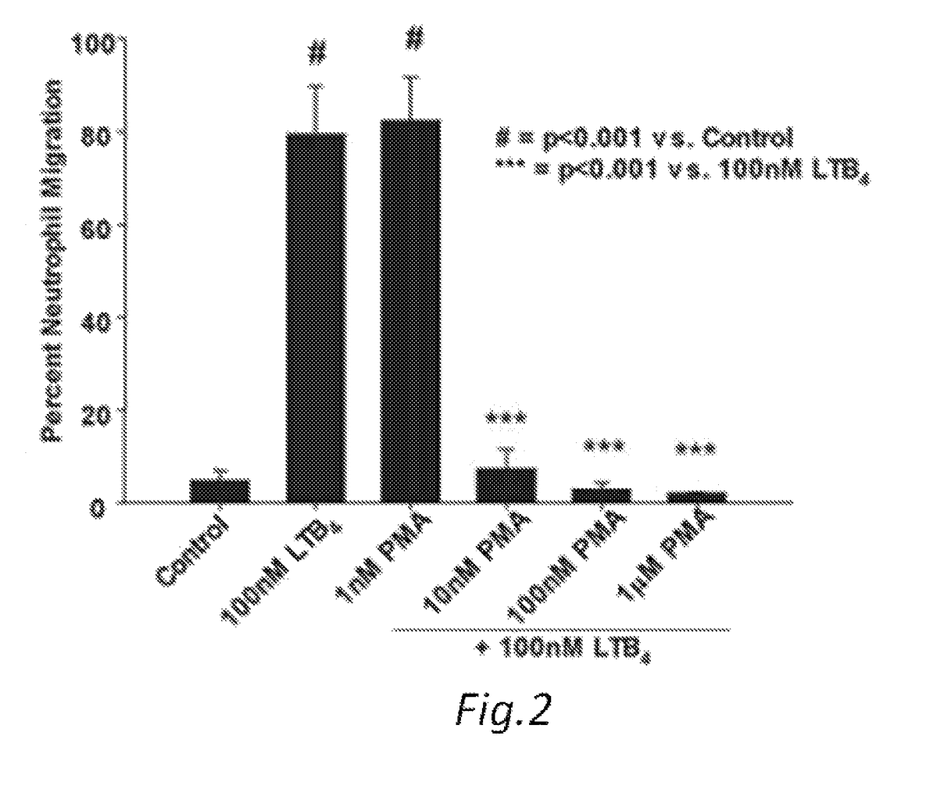
FIG. 2 is a graph that depicts a dose dependent effect of PMA on neutrophil migration.

Turning next to FIG. 2, FIG. 2 graphically depicts a dose dependent response of PMA on neutrophil migration. The chemotactic agent 100 nM $LTB_4$ significantly increased neutrophil migration (*p<0.001) across confluent HMECs grown on transwells compared to control after 3 h incubation. Pretreatment with 100 nM, 10 nM, or 1 nM PMA (1 h) reduced $LTB_4$ induced migration in a dose dependent manner (*p<0.001). Lower concentrations of PMA (1 nM) had no effect on $LTB_4$ induced migration.

Figure 3:
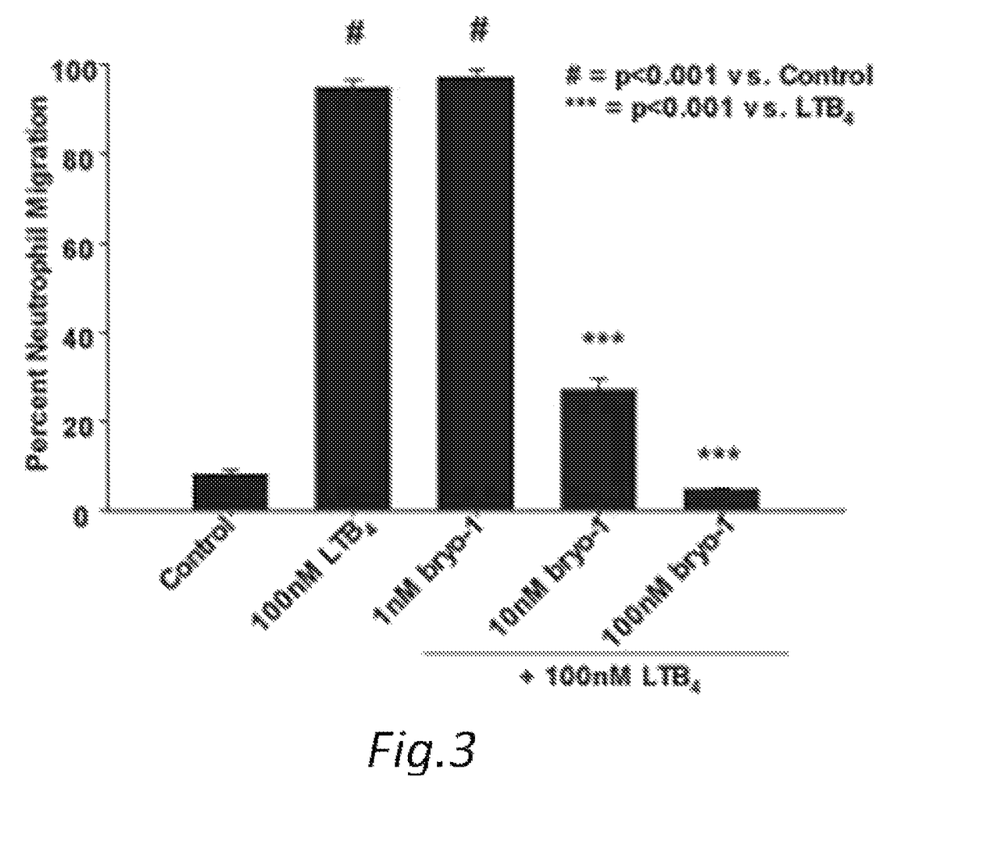
FIG. 3 is a graph that depicts a dose dependent response of Bryostatin-1 on neutrophil migration.

And, now turning to FIG. 3, FIG. 3 graphically depicts a dose dependent response of Bryostatin-1 on neutrophil migration. The chemotactic agent 100 nM $LTB_4$ significantly increased neutrophil migration (*p<0.001) across confluent HMECs grown on transwells compared to control after 3 h incubation. Pretreatment with either 100 nM ($10^{-7}$M) or 10 nM ($10^{-8}$M) Bryostatin-1 (for 1 h) reduced $LTB_4$ induced migration in a dose dependent manner (*p<0.001).

Figure 4:
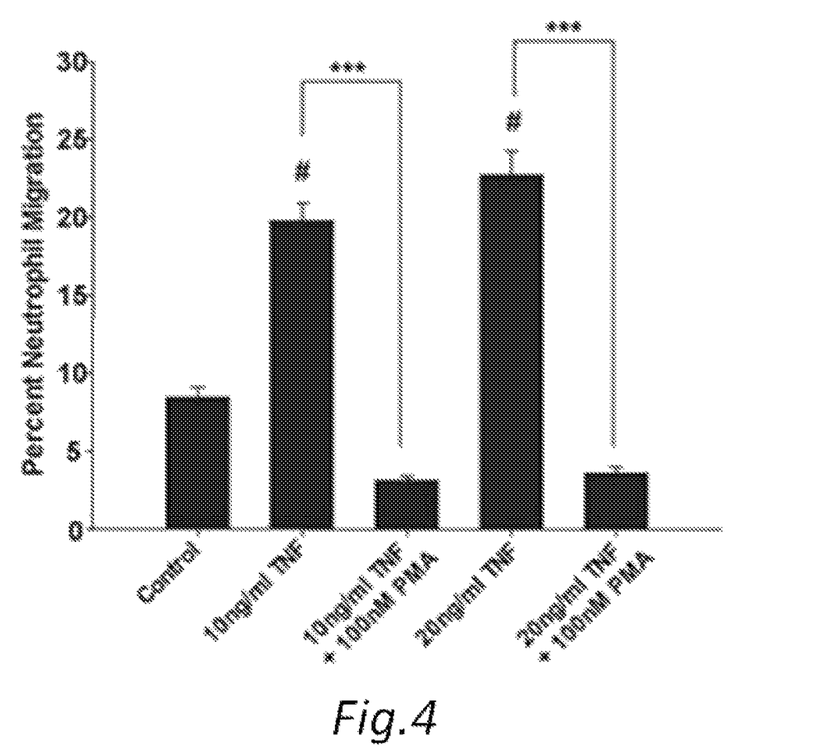
FIG. 4 is a graph depicting the effect of PMA on TNF-α induced neutrophil migration.

FIG. 4 graphically depicts the effect of PMA on TNF-α induced neutrophil migration. Endothelial activation induced by a 24 h pretreatment with either 10 or 20 ng/ml TNF-α significantly increased neutrophil migration (p<0.05) across confluent HMEC monolayers grown on transwells. This TNF-α induced TEM was totally attenuated by 1 hour pretreatment with 100 nM PMA (***p<0.001).

Figure 5:
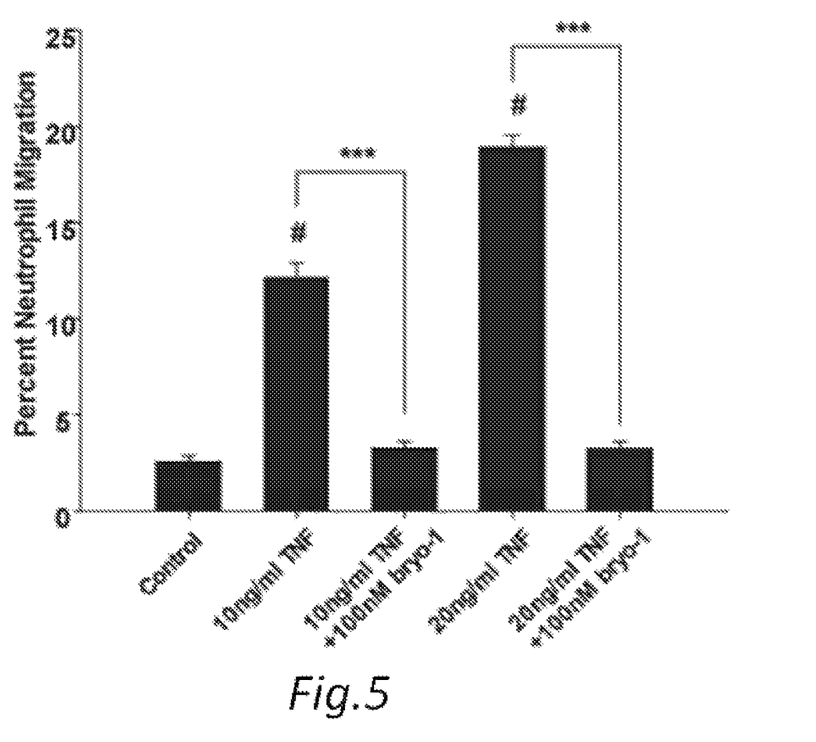
FIG. 5 is a graph depicting the effect of Bryostatin-1 on TNF-α induced neutrophil migration.

Turning now to FIG. 5, FIG. 5 graphically depicts the effect of Bryostatin-1 on TNFα a induced neutrophil migration. Endothelial activation by a 24 h pretreatment with 10 or 20 ng/ml TNF-α significantly increased neutrophil migration (*p<0.05) across confluent HMEC monolayers grown on transwells. This TNF-α induced TEM was totally attenuated by a 1 hour pretreatment with 100 nM ($10^{-7}$M) Bryostatin-1 (***p<0.001).

Figure 6:
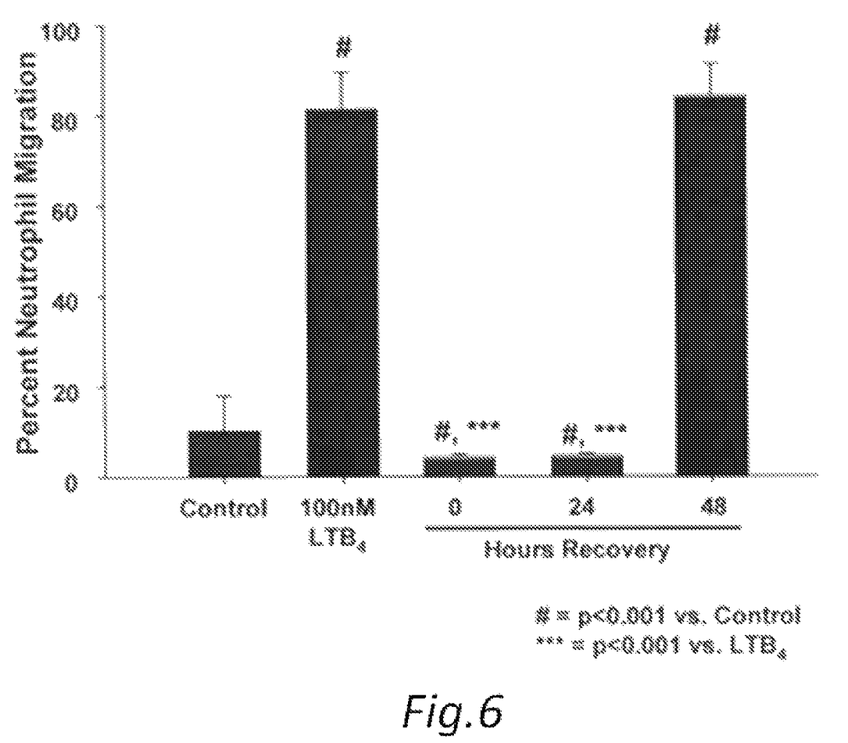
FIG. 6 is a graph that depicts PMA protects against $LTB_4$ induced PMN chemotaxis at least 48 h after pretreatment.

FIG. 6 graphically depicts protection against $LTB_4$ induced PMN TEM with PMA up to 48 h after pretreatment. HMECs were pretreated for 1 h with PMA and washed with HBSS three times to remove PMA prior to replacement of culture medium. Neutrophil migration studies were then performed at 0, 24, or 48 hours. Migration was stimulated by adding 500,000 neutrophils to the top well and 100 nM $LTB_4$ to the lower well at 0, 24, and 48 hours after PMA pretreatment. The chemotactic agent $LTB_4$ significantly increased neutrophil migration (*p<0.001) compared to controls after 3 h incubation. PMA (100 nM, ($10^{-7}$M) reduced $LTB_4$ induced migration up to 48 hours after 1 h of endothelial-specific pretreatment (*p<0.001).

Figure 7:
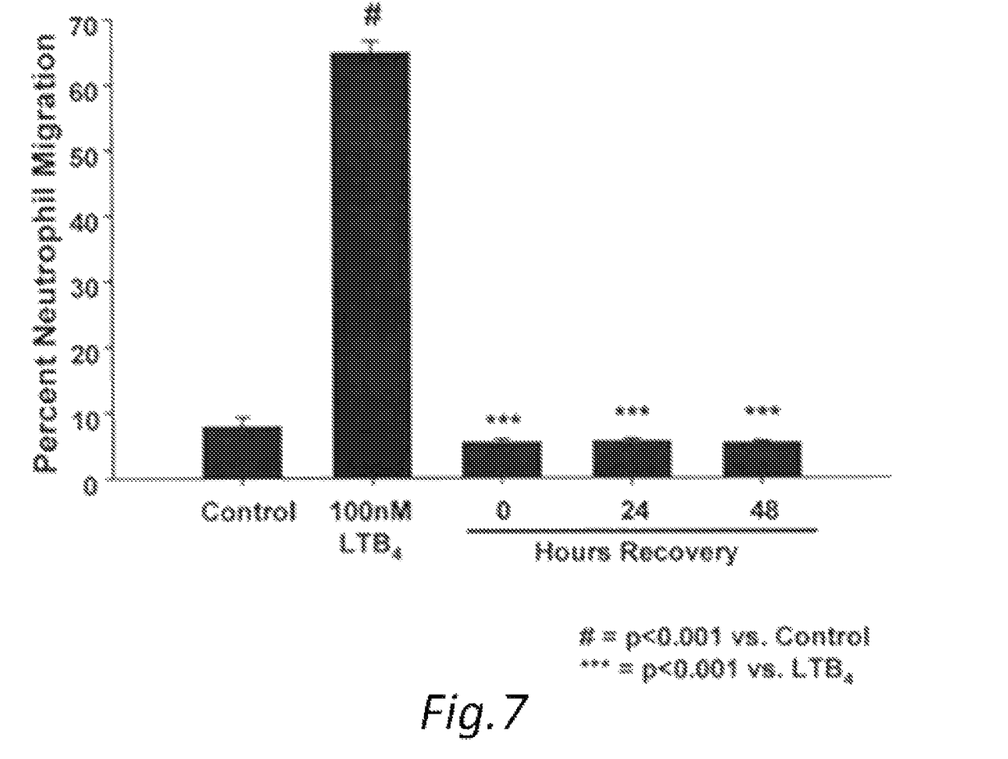
FIG. 7 is a graph that depicts Bryostatin-1 protects against $LTB_4$ induced PMN TEM for at least 48 h after pretreatment.

Referring now to FIG. 7, FIG. 7 graphically depicts protection from $LTB_4$ induced PMN TEM with Bryostatin-1 up to 48 hours after pretreatment. HMECs were pretreated for 1 h with Bryostatin-1 and washed with HBSS three times to remove Bryostatin-1 prior to replacement of culture medium. Neutrophil migration studies were then performed at 0, 24, or 48 hours. Migration was stimulated by adding 500,000 neutrophils to the top well and 100 nM $LTB_4$ to the lower well at 0, 24, and 48 hours after Bryostatin-1 pretreatment. The chemotactic agent $LTB_4$ significantly increased neutrophil migration (*p<0.001) compared to control after 3 hours of incubation. Bryostatin-1 (100 nM) reduced $LTB_4$ induced migration up to 48 hours after 1 hour endothelial pretreatment (*p<0.001).

Figure 8:
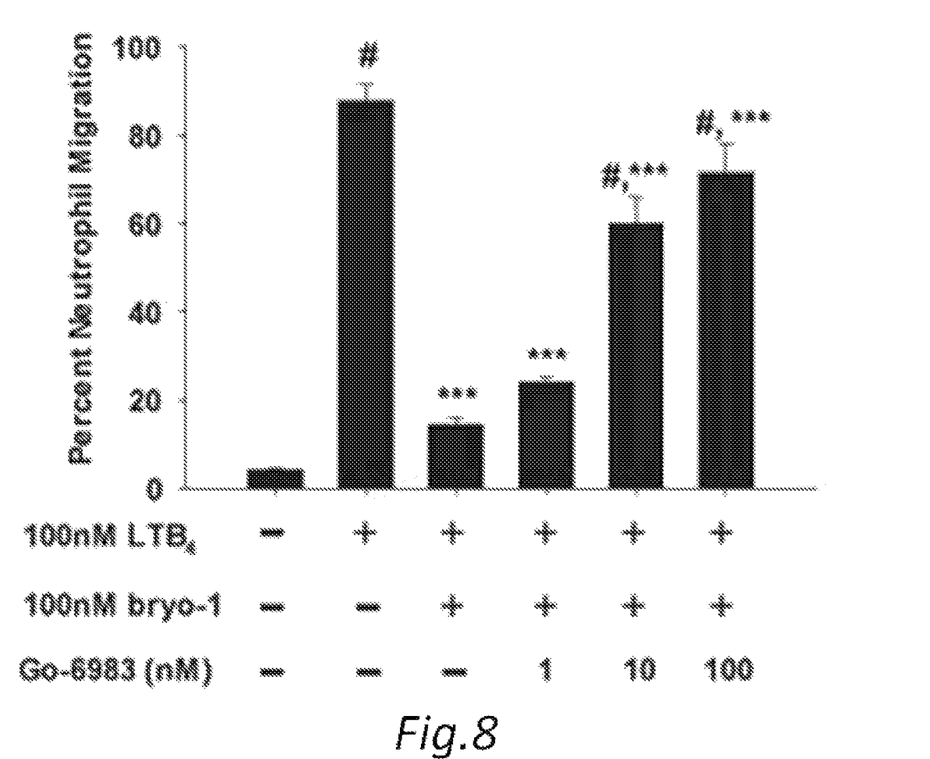
FIG. 8: is a graph that demonstrates that Bryostatin-1 mediated protection against $LTB_4$ induced PMN TEM is dose dependently reversed by the PKC-δ antagonist G0-6983 at 1, 10 and 100 nM.

FIG. 8 graphically depicts protection from $LTB_4$ induced PMN TEM with Bryostatin-1 is dose dependently reversed by G0-6983 at 1, 10 and 100 nM. HUVEC were pretreated with G0-6983, a PKC inhibitor with dose dependent specificities for classical vs. novel PKC isoforms for 30 minutes prior to addition of Bryostatin-1 (100 nM) to block neutrophil migration. Lower concentrations of G0-6983 (1-10 nM) have been shown to inhibit classical PKC isoforms, while higher concentrations (10-100 nM) have been suggested to inhibit novel PKC isoforms e.g. PKC-δ and -ε. Neutrophil migration towards 100 nM $LTB_4$ was initiated by adding $LTB_4$ to the lower well. The chemotactic agent $LTB_4$ significantly increased neutrophil migration (# p<0.001) compared to controls after 3 h incubation and was reversed by 100 nM Bryostatin-1 (***p<0.001). This Bryostatin-1 mediated reduction in migration towards $LTB_4$ was prevented by a prior endothelial pretreatment with 10 or 100 nM GO6983 (# p<0.05), but not by 1 nM GO6983.

Figure 9:
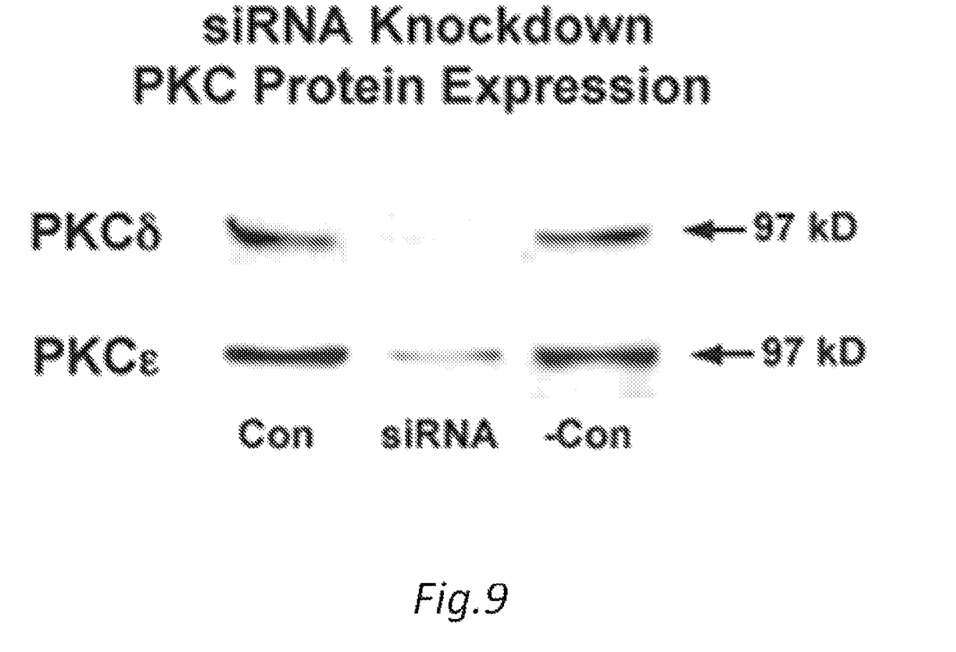

Turning now to FIG. 9, FIG. 9 graphically depicts how siRNA knockdown of specific PKC isoforms (PKC-δ) can be used to demonstrate the particular PKC isoform mediating the trans endothelial migration suppression mediated by Bryostatin-1. Because studies in FIG. 8 could not discriminate between PKC-δ and PKC-ε isoforms mediating the effect of Bryostatin-1, we knocked down individual isoforms using siRNA technology. In order to verify that we could knock down particular isoforms of PKC, specifically PKC-δ and PKC-ε isoforms in HUVEC, siRNA which selectively bind to and eliminate human PKC-δ and PKC-ε mRNAs were nucleofected into HUVEC prior to migration studies. FIG. 9 shows that PKC-δ nucleofection (top row middle lane) completely eliminated PKC-δ expression, while a control siRNA (top row, right lane) did not. Similarly, HUVEC were nucleofected with PKC-ε siRNA which also lead to a significant reduction in PKC-ε (bottom row middle lane) while a control siRNA (bottom row, right lane) did not. HUVEC cells treated using these approaches were then subjected to chemotaxis studies with Bryostatin-1 to elucidate the mechanism of Bryostatin-1 mediated inhibition of $LTB_4$ induced PMN migration.

Figure 10:
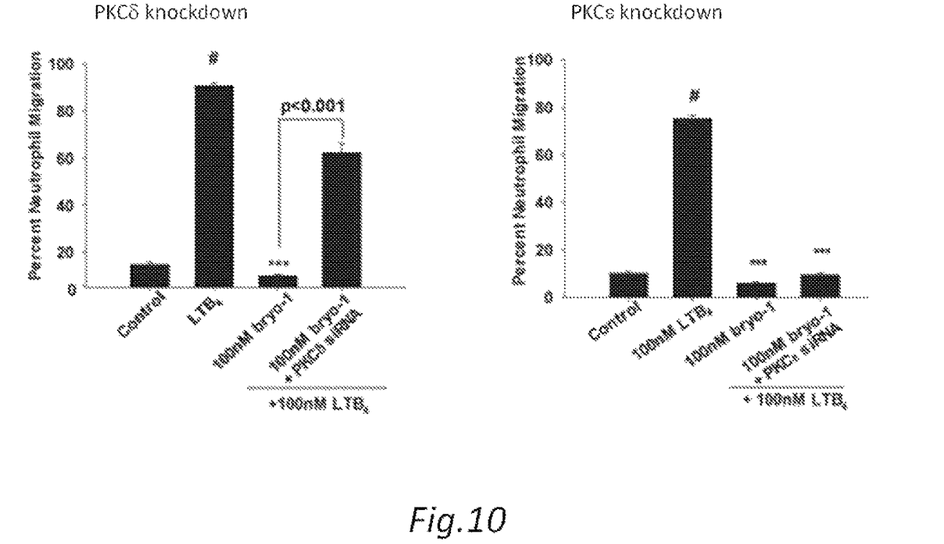

FIG. 10 graphically depicts that Bryostatin-1 will not inhibit $LTB_4$ mediated neutrophil migration in PKC-δ nucleofected HUVEC, but still suppresses migration in PKC-ε nucleofected HUVEC. FIG. 10 (left panel) shows that compared to the normal level of migration induced by $LTB_4$ (# p<0.05), 100 nM Bryostatin-1 significantly suppressed $LTB_4$ induced migration. Because PKC-δ nucleofection significantly suppresses PKC-δ expression (FIG. 9) and also significantly restored neutrophil migration previously blocked by Bryostatin-1 (p<0.001 vs. 100 nM Bryostatin-1), this result demonstrates the dependence of Bryostatin-1 suppression on the PKC-δ isoform in endothelial cells and not other cell types. PKC-ε nucleofection (FIG. 10, right panel) shows that Bryostatin-1 inhibition of $LTB_4$ induced migration was not prevented by PKC-ε suppression (shown in FIG. 9). Therefore, these data are only consistent with Bryostatin-1 mediated suppression of neutrophil chemotaxis as being mediated by the PKC-δ isoform, and not by PKC-ε.

These studies identify a role for a previously unreported second messenger in the prevention of both Type I and Type II neutrophil infiltration. We have shown that PKC activation, more specifically PKC-δ activation can totally abolish neutrophil TEM in response to an $LTB_4$ gradient, or across TNF-α activated endothelial cells. In addition, we show that a short-term treatment to activate PKC-δ can protect against chemotaxis-induced neutrophil infiltration for at least 48 hours after initial exposure to the drug and not requiring the persistent presence of the drug treatment. We also found an abolition of neutrophil trans endothelial migration across HUVECs and HMECs towards both an $LTB_4$ gradient and endothelial TNF-α stimulation using two different PKC activators. These levels of reduction were similar only to those reported here for the blockade of intracellular $Ca^{++}$ release. This is interesting, because $Ca^{++}$ has been suggested by numerous investigators to be the first second messenger increased upon neutrophil adhesion to an endothelial monolayer. While no studies have shown alterations in PKC activity upon neutrophil adhesion to an endothelial monolayer, endothelial PKC activation is just as potent as $Ca^{++}$ inhibition in reducing neutrophil TEM towards an $LTB_4$ gradient and in response to endothelial activation by TNF-α. It is possible that neutrophil adhesion to the endothelium does not result in any alterations in PKC activity, but it has been shown that activation of particular isoforms, including PKC-α, -β, -Y, and -δ can result in alterations in endothelial barrier function. This alteration could be involved in regulating neutrophil passage through the endothelial monolayer.

Isoforms of PKC are shown to be involved in numerous cellular processes ranging from apoptosis to cell proliferation and differentiation. There are three described PKC subgroups categorized by their structure, modes of activation, and their regulation including the conventional (-α, -β1, -β11, -Y), novel (-δ, -ε, -η, -θ) and atypical (-ζ and -ι/λ) isoforms. Activation of PKC has long been accepted as a mechanism responsible for reduced endothelial barrier integrity induced by numerous mediators including thrombin, VEGF, $H_2O_2$, glucose, and phorbol esters. While the exact mechanism of PKC mediated permeability has not been elucidated, PKC activation has been shown to target the endothelial cytoskeleton resulting in MLC phosphorylation and actin polymerization. In addition PKC activation has been shown to disassemble VE-cadherin, and induce reorganization of focal adhesions.

We have demonstrated a role for PKC in cadherin endocytosis and increased endothelial permeability. Many distinct isoforms of PKC have been implicated in the induction of endothelial permeability, though there seems to be no general consensus on the precise isoform.

The phorbol ester PMA (phorbol myristate acetate), a pan PKC activator, has been shown in numerous studies to decrease trans endothelial resistance (TER) in several types of endothelial and epithelial cells. This is due to the activation and translocation of the PKC-α isoform and not PKC-δ or -ε. Also, the treatment of porcine aortic endothelial cells with specific antisense oligodesoxynucleotides against PKC-α reduces enhanced permeability induced by glucose. A role for the β isoform has also been implicated in increased permeability caused by high glucose and PMA. The PKC-α inhibitor hypocrellin A and the PKC-β inhibitor LY379196 both reduced this increased permeability with a greater effect seen with PKC-α inhibition. Numerous studies have supported a role for PKC-α in thrombin and PMA-mediated permeability in HUVECs, TNF-α-induced permeability in pulmonary microvessel endothelial cells, and lysophosphatidylcholine (LPC)-stimulated permeability in human dermal endothelial cells highly implicating PKC-α as an important mediator of endothelial barrier function.

PKC-δ and -η have been linked to hyper permeability of pulmonary microvascular endothelial cells as a result of PMA treatment. It is important to note that these last findings are in pulmonary endothelia and may represent a unique mechanism to the rest of the vasculature. In fact, an overexpression of PKC-α significantly elevated permeability in thrombin stimulated rat epididymis microvascular endothelial cells, while PKC-δ over-expression significantly blunted thrombin-induced increases in permeability. This data further supports the role of PKC-α in permeability, and suggests that PKC-δ may have beneficial effects to decrease solute permeability which are anatomy specific. This represents a possible mechanism for the reduction in vascular injury through enhancement of endothelial barrier function induced by activation of PKC-δ.

In addition, PKC-δ has been shown to modulate activation of NF-κKB, a transcription factor that plays a key role in regulating both immune and inflammatory responses. While PKC-δ activation via thrombin has been shown to increase ICAM-1 expression, we have shown that Bryostatin-1 protects against $LTB_4$ induced migration for up to 48 hours and protects against TNF-α induced migration a factor known to also promote NF-κB activity and ICAM-1 expression. This suggests that Bryostatin-1 against neutrophil TEM independent of adhesion mechanisms.

Because PMA is a potent carcinogen, while Bryostatin-1 has been used to suppress carcinogenesis, we chose to primarily focus on the effects of Bryostatin-1 in reducing neutrophil TEM. Bryostatin-1 is a macrocyclic lactone isolated from the marine invertebrate *Bugula neritina* that activates PKC in a unique way to phorbol esters in that it more potently activates the PKC-δ and -ε isoforms. Bryostatin-1 is currently in Phase II trials used in combination with other drugs for the treatment of a variety of cancers. So far the only major side effects found to be associated with Bryostatin-1 use are myalgias, nausea, and vomiting; no cardiovascular disturbances or evidence of edema have been observed. Continual Bryostatin-1 treatment results in down-regulation in most PKC isoforms (-α, -β, -ε), however, numerous studies have suggested that PKC-δ is not down-regulated by continuous Bryostatin-1 administration and can rather maintain PKC activation. Therefore, based on persistent PKC-δ activation, Bryostatin-1 can be translated into use for other disorders benefiting from consistent PKC-δ activation including acute inflammatory states. Therefore, Bryostatin-1 may protect against inflammatory injury by down-regulating PKC-α and activating PKC-δ producing beneficial barrier effects (anti-edema, anti-inflammatory).

Bryostatin-1 enhances barrier function and inhibits barrier loss induced by TNF-α in T84 intestinal epithelia. The fact that Bryostatin-1 does not impair endothelial barrier might indicate that the isoforms of PKC it activates do not disturb barrier or may potentially improve it.

Therefore, we have shown that PKC-δ activation protects against type I ($LTB_4$ induced) and type II (TNF-α) induced neutrophil trans endothelial migration in vitro.

According to the invention, in order to produce protection of tissues, the vasculature is exposed to concentrations of Bryostatin-1 to achieve plasma levels of $10^{-7}$M or 100 ng/mL. A preferred Bryostatin-1 concentration is therefore about 100 ng/ml. Results obtained with healthy subjects and cancer patients have shown no adverse effects to even higher dosing ranges.

The transplantation solution would similarly contain Bryostatin-1 up to $10^{-7}$M, in which the transplantation solution is UW transplantation buffer solution, Plegisol or other organ transplantation harvesting/storage buffers.

In a general manner, for the implementation of the method according to the invention, the minimal tissue incubation stage is carried out at ambient temperature, by perfusion loading the organ with this quantity of Bryostatin-1, and according to the duration of the organ transportation, allowing the desired vascular protection to be obtained.

In a tissue or systemic embodiment of the invention, Bryostatin-1 is injected, inhaled, applied or aspirated to exposure select regions of the vasculature. In the case of dermal, peritoneal or alveolar application, concentrations in excess or below $10^{-7}$ M will be used depending on the condition being treated. By way of example, Bryostatin-1 can be mentioned as an activator of PKC-δ.

The invention also relates to diagnostic kits or sets for the implementation of the test defined above. These kits are characterized in that they comprise, with instructions for use, Bryostatin-1 as defined above, with, if appropriate, receptacles and reagents, these reagents being chosen from activators and/or inhibitors of PKC.

Therefore, the invention provides means of tissue protection which are potent, lasting and non-invasive, allowing the rapid and economical treatment of these diseases to be carried out.

EXAMPLES

Reagents and Abs:

$LTB_4$, PMA, and Bryostatin-1 were purchased from Biomol (Plymouth, Pa.). Alamar blue solution was from Biosource International (Camarillo, Calif.). PKC-ε siRNA SMARTpool, non-specific control siRNA pool, and anti-PKC-ε monoclonal antibodies were obtained from Upstate Cell Signaling (Lake Placid, N.Y.). PKC-δ siRNA (Duplex 2) was purchased from Molecular (Sterling, Va.) and the anti-PKC-δ polyclonal antibody was from Chemicon (Temecula, Calif.). Nucleofection reagents were obtained from Amaxa (Gaithersburg, Md.).

Subjects:

The procedure used to obtain human neutrophils was approved by the Institutional Review Board for Human Research at the Louisiana State University Health Sciences Center. Each subject provided written consent for participation in the study.

Cell Culture:

HMECs were a generous gift from Dr. Francisco Candal (Centers for Disease Control), and are derived from the subcutaneous microvasculature. HMECs were maintained in MCDB-131 supplemented with 10% FCS, 1% antibiotic antimycotic, 10 ng/ml EGF, and 1 pg/ml hydrocortisone. The cell cultures were incubated at 37° C. in a humidified atmosphere with 7.5% $CO_2$ and expanded by brief trypsinization (0.25% trypsin in phosphate-buffered saline containing 0.02% EDTA). HMECs were seeded onto 8 µm inserts for migration assays and 48-well plates for endothelial viability studies. Human umbilical vein endothelial cells (HUVECs) were harvested from umbilical cords by 0.25% collagenase treatment for 20 min at 37° C. HUVECs were maintained in Endothelial Growth Medium (EGM) supplemented with Bovine Brain Extract. The cell cultures were incubated at 37° C. in a 100% humidified atmosphere with 5% $CO_2$ and expanded by brief trypsinization. Primary passage HUVEC were seeded onto fibronectin coated (25 µg/ml) 8 µm inserts for migration assays and 48-well plates for endothelial viability studies. Culture medium was replaced every second day. Cells were identified as endothelial cells by their cobblestone appearance at confluency, positive labeling with acetylated low density lipoprotein labeled with 1,11-dioctadecyl-1 3,3,31,31,3-tetramethylindocarbocyanine perchlorate (Dil-Ac-LDL; Biomedical Technologies, Inc.) and mouse antihuman factor VIII (Calbiochem, San Diego, Calif.).

Neutrophil Isolation:

Neutrophils were isolated using a Ficoll gradient. Whole blood was taken from human donors, and 5 ml was layered on top of two layers of Histopaque. Tubes were spun at 2,100 rpm for 40 min. The neutrophil layer was added to cold PBS and respun at 2,100 rpm for 5 min. Supernatant was removed and neutrophils were suspended in a fixed amount of PBS to determine cell count. Cells were kept on ice until assays were performed.

Migration Assays:

At confluency HMECs were treated for 1 h at 37° C. with Bryostatin-1 (10 nM, 100 nM) in MCDB-131 media or MCDB-131 media alone. Inserts were washed three times with Hank's Balanced Salt Solution (HBSS) (to eliminate drug effects on the neutrophils) and placed in a new plate containing either 500 µL 100 nM $LTB_4$, or HBSS alone for control. 500 µL HBSS was then added to the top well and spiked with 500,000 neutrophils. For TNF-α experiments, HMECs were left in 20 ng/ml TNF-α in MCDB-131 for 24 h TNF-α was removed and HMECs washed three times. HMECs were treated for 1 h with Bryostatin-1 in endothelial growth medium (EGM) (10 nM, 100 nM). The drug was removed and cells were washed three times. 500 µL HBSS was added to both upper and lower chambers and spiked with 500,000 neutrophils. Neutrophils were allowed to migrate for 3 h at 37° C. Migration was stopped by removing the inserts and migration was measured using the myeloperoxidase (MPO) assay.

Time Course Assays:

At confluency, HUVECs were treated for 1 h at 37° C. with Bryostatin-1 (10 nM, 100 nM) in EGM or EGM alone. Inserts were washed three times with HBSS (to reduce drug effects on the neutrophils) and migration assays were ran at t=0, 24, or 48 h. After time elapsed, HUVECs were placed in a new plate containing either 500 µL 100 nM $LTB_4$ or HBSS alone for control. 500 µL HBSS was then added to the top well and spiked with 500,000 neutrophils. Neutrophils were allowed to migrate for 3 h at 37° C. Migration was stopped by removing the inserts and migration was measured using the MPO assay.

Neutrophil Transendothelial Migration (TEM) Restoration Studies:

HUVECs were pretreated with Go-6983 (1, 10, 100 nM), or Go-6976 (1, 10, 100 nM) for 30 minutes, then spiked with 100 nM Bryostatin-1 for 1 hour. HUVECs previously nucleofected with PKC-δ, -ε, or control siRNA were just treated in Bryostatin-1 for 1 hour. HUVECs were washed three times and placed in a new plate containing either 500 µL 100 nM $LTB_4$, or HBSS alone for control. Neutrophils were allowed to migrate for 3 h at 37° C. Migration was stopped by removing the inserts and migration was measured using the MPO assay.

Myeloperoxidase Assay:

Neutrophil migration was measured using myeloperoxidase (MPO) analysis. Cell culture inserts were first removed and plates were spun at 1,500 RPM for 5 min. The supernatant was removed, and MPO activity was measured using TMB/peroxide as chromogen. The reaction was stopped with sulfuric acid and absorbance was read at 450 nm using a microplate reader. All experiments were performed n=6. Data was expressed as "% neutrophil migration", which allowed cumulative statistical analysis to be done and account for unpreventable batch-to-batch variations.

Viability Assay.

The Alamar blue assay was used to determine endothelial viability after pharmacological intervention. Alamar blue contains a REDOX indicator that results in a color change upon chemical reduction by cellular metabolic activity. Endothelial cells were treated with Bryostatin-1 (100 nM) for 1 h and washed three times with HBSS. Alamar blue (10%) in media was added for 2.5 h at T=0, 24, or 48 hours after drug treatment and the ratio of absorbances (570-600 nm) was measured to determine metabolic activity.

siRNA.

Optimum nucleofection parameters were determined using nucleofection of a control vector pmaxGFP. Using fluorescence microscopy and flow cytometry, 2 µg vector/500,000 cells nucleofected yielded the highest nucleofection (data not shown). HUVECs were grown to 70% confluency, trypsinized, and then counted. 500,000 cells were spun down 5 min at 1500 rpm and resuspended in 100 µL HUVEC nucleofector solution and 2 µg PKC-δ, PKC-ε, or control siRNA. Suspensions were transferred to an Amaxa certified cuvette and nucleofected using a Nucleofector Device that uses a unique combination of electrical parameters to deliver the siRNA directly to the cell nucleus. 500,000 nucleofected HUVECs were then transferred either to one fibronectin coated 8 µm insert, or one fibronectin coated well in a 12-well plate. Migration assays and Western blotting was performed 24 hours after nucleofection for optimal knockdown.

Statistical Analysis:

All values are expressed as means±standard error (SE). Data were analyzed using a one-way ANOVA with Bonferroni corrections for multiple comparisons. Probability (p) values of <0.05 were considered significant.

Example 1

Second Messenger Reduction of Neutrophil TEM in Response to $LTB_4$

The time scale of neutrophil adhesion to and migration through a HMEC monolayer is represented in FIG. 1. A 100 nM concentration of $LTB_4$ induces maximal adhesion at 1 hour accompanied by only a small increase in migration. As adhesion begins to decrease there is a corresponding increase in neutrophil migration. By 90 minutes neutrophil migration is almost maximal and neutrophil adhesion has returned to baseline. To determine novel endothelial second messengers that could inhibit neutrophil trans endothelial migration, endothelial cells were treated with a panel of pharmacological inhibitors and activators and alterations in neutrophil migration in response to $LTB_4$ were observed.

Confluent HMEC monolayers were plated on 48-well plates for adhesion studies, transwells for migration studies, and pretreated with a variety of pharmacological inhibitors and activators for 1 hour. Monolayers were washed three times with HBSS to remove all drug effects on the endothelium. To initiate migration, 100 nM $LTB_4$ was added to the lower compartment and 500,000 neutrophils were added to the upper compartment and allowed to migrate for 3 h. For adhesion assays, $LTB_4$ was added along with 500,000 neutrophils and allowed to adhere for 1 h (time of max. adhesion as determined in FIG. 1). In all experiments $LTB_4$ induced migration was significantly greater than control migration (p<0.001). The data are shown as % change in migration and adhesion as assessed by MPO assay. All values are expressed as means±SE. Data were analyzed using a one-way ANOVA with Bonferroni corrections for multiple comparisons. Probability (p) values of <0.05 were considered significant. *p<0.001 vs. $LTB_4$; p<0.01 vs. $LTB_4$; **p<0.05 vs. $LTB_4$; n=4 for all experiments.

While some of these results including inhibition of intracellular $Ca^{++}$ release, protein kinase A (PKA) activation, MLCK inhibition, and disruption of microfilaments have previously been investigated in relation to their effects on neutrophil migration, most of the other drugs have not been studied. In fact our most robust novel results on the inhibition of neutrophil migration were in response to endothelial PKC activation with Bryostatin-1. We determined that inhibition of intracellular $Ca^{++}$ release, disruption of microfilaments, exogenous nitric oxide, alterations in tyrosine phosphorylation, PI-3 kinase inhibition and finally activation of PKC in the endothelium alone reduced polymorphonuclear leukocyte (PMN) TEM.

In addition, because no endothelial cell adhesion molecule has been determined to play a role in Type I (neutrophil-mediated) neutrophil migration, we also screened a number of endothelial adhesion molecules and integrins and determined that CD99, LSP-1, ocv133, and 131 integrin played no apparent role in mediating neutrophil TEM towards an $LTB_4$ gradient. However, PECAM-1 slightly, but significantly decreased neutrophil migration towards an $LTB_4$ gradient (%).

Example 2

Type I and II Neutrophil TEM is Attenuated by PKC Activators

As shown in FIGS. 2 and 3, neutrophil migration was dramatically increased in response to a 100 nM $LTB_4$ chemoattractant gradient in HMECs.

This increase was dose-dependently reduced upon 1 hour PMA or Bryostatin-1 pretreatment (FIGS. 2 and 3). Lower doses of PMA and Bryostatin-1 (1 nM) did not reduce PMN TEM, however, higher doses attenuated neutrophil TEM to levels below that of basal migration (100 nM). Because there are two types of neutrophil migration that are differentially regulated, we wanted to determine if PKC activators could also block neutrophil TEM induced by a cytokine. HMEC TNF-α stimulation for 24 hours induced significant increases in neutrophil migration (FIGS. 4 and 5).

Both PMA (100 nM) and Bryostatin-1 (100 nM) additionally attenuated Type II migration induced by 24 h treatment with TNF-α (10, 20 ng/ml) (FIGS. 4 and 5). Also, PMA and Bryostatin pretreatments reduced migration induced by a combination of 24 h TNF-α pretreatment and a 100 nM $LTB_4$ gradient (data not shown). Neither PMA, nor Bryostatin-1 reduced $LTB_4$ induced adhesion to the endothelial monolayer, suggesting that the effects of PMA and Bryostatin-1 were directly through alterations in PMN migration (data not shown). In addition, a single 1 h 100 nM PMA pretreatment maintained a reduction in $LTB_4$ induced migration up to 48 h in HUVECs (data not shown) and 24 h in HMECs, while 1 h 100 nM Bryostatin pretreatment maintained the reduction in migration for 48 h in both cell types (FIGS. 6 and 7). These treatments had no effect on HMEC, or HUVEC viability at any given time point (1, 24, 48 h) with the exception of a slight but significant reduction in viability of HUVECs 48 h after a single 1 h treatment with 100 nM PMA. However, because PMA is a tumor promoter, while Bryostatin-1 is well described as a tumor suppressor, Bryostatin-1 represents a highly active and safe alternative to other PKC activators currently described in the literature including benzolactams and indolactams.

Example 3

Activation of PKCs Reduces Neutrophil Migration in Response to $LTB_4$

To insure that PMA and Bryostatin-1 effects were dependent on PKC activation, we tested various PKC inhibitors in the restoration of PMN TEM in response to $LTB_4$. While Rottlerin (a PKC-δ inhibitor), GF10923X (pan PKC inhibitor more potent for -α, -β1, -β11, -Υ more potently), GO-6976 (inhibits PKC-α and -β with no effect on -δ, -ε, -ζ) and staurosporine (pan PKC inhibitor) did not restore PMN TEM, Go-6983 dose dependently restored neutrophil migration in response to $LTB_4$ (FIG. 8). It has been suggested that different concentrations of Go-6983 inhibit different PKC isoforms. Lower concentrations (1 nM) have been suggested to inhibit classical PKC isoforms, while higher concentrations (10 nM) have been suggested to inhibit novel PKC isoforms.

Therefore we choose to investigate the roles of PKC-δ and PKC-ε activation in inhibiting neutrophil TEM. PKC-δ and -ε siRNA were used to determine each isoforms role in this process. As assessed by FACS for GFP and control nucleofected HUVECs, 2 μg nucleofected GFP resulted in a 60% expression of GFP in HUVECs versus 0.48% in control nucleofected cells. Therefore nucleofection of HUVECs with siRNA should reduce PKC expression in at least 60% of nucleofected cells. PKC-δ and -ε siRNA nucleofection significantly reduced both PKC-δ and -ε expression as shown by Western blot (FIG. 9). Surprisingly, PKC-ε siRNA nucleofection did not restore $LTB_4$ induced migration after either PMA or Bryostatin-1 pretreatment demonstrating that the effects of PMA and Bryostatin-1 were not mediated by activation of the PKC-ε isoform (FIG. 10). However, because PKC-δ siRNA nucleofection restored the normal level of neutrophil trans endothelial migration induced by $LTB_4$ these studies prove that Bryostatin-1 blocks neutrophil migration across endothelium by activating PKC-δ specifically in endothelial cells and not other cell types (FIG. 10). This suggested that PKC-δ activation is at least partially responsible for Bryostatin-1 effects on neutrophil migration induced by $LTB_4$.

The invention claimed is:

1. A dosage form for treating transplantation injury comprising an effective amount of Bryostatin-1, Bryostatin-1 analog or a pharmaceutically acceptable salt thereof to reduce or prevent induced neutrophil trans endothelial migration wherein said dosage form is for administration to a human or animal in need thereof; wherein said dosage form comprises saturated polyalkylene glycol glyceride; and wherein said effective amount in the organ is a plasma concentration is about $10^{-7}$ M.

2. The dosage form of claim 1 wherein said dosage form is a solid oral dosage form.

3. The dosage form of claim 1 wherein said polyalkylene glycol glyceride is a mixture of polyalkylene esters of one or more eight carbons to eighteen carbons saturated fatty acids with glycerol.

4. The dosage form of claim 3 wherein said polyalkylene glycol is a polyethylene glycol having a molecular weight of 1000 to 2000 daltons.

5. The dosage form of claim 4 wherein said polyalkylene glycol is a polyethylene glycol having a molecular weight of 1400 to 1600 daltons.

6. The dosage form of claim 2 wherein said Bryostatin-1, Bryostatin-1 analog or pharmaceutically acceptable salt thereof is present in said oral dosage form in an amount of 1 to 30% by weight.

7. The dosage form of claim 2 wherein said Bryostatin-1, Bryostatin-1 analog or pharmaceutically acceptable salt thereof is present in said oral dosage form in an amount of 10 to 20% by weight.

8. The dosage form of claim 2 wherein said Bryostatin-1, Bryostatin-1 analog or pharmaceutically acceptable salt thereof is present in said oral dosage form in an amount of 2 to 25% by weight.

9. The dosage form of claim 1 wherein said dosage form is a pharmaceutical parenteral formulation.

10. The dosage form of claim 9 wherein said pharmaceutical parenteral formulation comprises polyalkylene glycol glyceride.

11. The dosage form of claim 9 wherein said polyalkylene glycol glyceride is a mixture of polyalkylene esters of one or more eight carbons to eighteen carbons saturated fatty acids with glycerol.

12. The dosage form of claim 11 wherein said polyalkylene glycol is a polyethylene Glycol having a molecular weight of 1000 to 2000 daltons.

13. The dosage form of claim 12 wherein said polyalkylene glycol is a polyethylene glycol having a molecular weight of 1400 to 1600 daltons.

14. The dosage form of claim 9 wherein said Bryostatin-1, Bryostatin-1 analog or pharmaceutically acceptable salt thereof is present in said pharmaceutical formulation in an amount of 0.00005 to 0.5% by weight.

15. The dosage form of claim 9 wherein said Bryostatin-1, Bryostatin-1 analog or pharmaceutically acceptable salt thereof is present in said pharmaceutical formulation in an amount of 0.001 to 0.1% by weight.

16. The dosage form of claim 9 wherein said Bryostatin-1, Bryostatin-1 analog or pharmaceutically acceptable salt thereof is present in said pharmaceutical parenteral formulation in an amount of 0.01 to 0.1% by weight.

17. The dosage form of claim 9 wherein said Bryostatin-1, Bryostatin-1 analog or pharmaceutically acceptable salt thereof is present in said pharmaceutical parenteral formulation as a dispersion in water having a concentration of 0.0005 to 0.5% by weight.

* * * * *